(12) United States Patent
Stern

(10) Patent No.: US 6,361,721 B1
(45) Date of Patent: Mar. 26, 2002

(54) METHOD OF FORMING TOOTH RESTORATION

(76) Inventor: Alvin L. Stern, P.O. Box 711333, Houston, TX (US) 77271-1333

( * ) Notice: Subject to any disclaimer, the term of this patent is extended or adjusted under 35 U.S.C. 154(b) by 0 days.

(21) Appl. No.: 09/311,387

(22) Filed: May 13, 1999

(51) Int. Cl.$^7$ ............................ A61C 5/10; A61C 13/083

(52) U.S. Cl. .............................. 264/19; 264/16; 106/35; 433/223

(58) Field of Search ............................ 264/16, 19, 20; 106/35; 433/223

(56) References Cited

U.S. PATENT DOCUMENTS

| | | | |
|---|---|---|---|
| 4,579,530 A | * | 4/1986 | McLaughlin ................ 433/223 |
| 5,298,200 A | * | 3/1994 | Kubo et al. ................... 264/19 |
| 5,470,231 A | * | 11/1995 | Stern ........................... 433/223 |
| 5,705,273 A | * | 1/1998 | Denry et al. ................. 428/410 |

* cited by examiner

Primary Examiner—James Derrington
(74) Attorney, Agent, or Firm—Bill B. Berryhill

(57) ABSTRACT

Refractory investment material and method for forming a positive replication of a tooth structure on which a high-alumina based porcelain tooth restoration is to be formed, the material being formed from a refractory powder which includes calcined alumina mixed with a liquid carrier comprising an aqueous colloidal dispersion of silicon dioxide. The method comprises the steps of: preparing a negative impression of the tooth structure on which a tooth restoration is to be placed; forming a positive replication of the tooth structure by pouring the mixture of refractory powder and aqueous dispersion into the negative impression; allowing the positive replication to harden; removing the positive replication from the negative impression for degassing and cooling; and coating the positive replication with a mixture of high-alumina porcelain in an aqueous carrier to form a core layer of porcelain on which subsequent layers of high-alumina porcelain may be applied.

11 Claims, 1 Drawing Sheet

METHOD OF FORMING TOOTH RESTORATION

BACKGROUND OF THE INVENTION

1. Field of the Invention

The present invention pertains to restoration of teeth. More specifically, the present invention pertains to materials and methods for forming porcelain tooth restorations for dental restoration of worn, damaged or malformed teeth.

2. Description of the Prior Art

There are many methods of restoring or repairing teeth. Practitioners in the field of restorative dentistry have developed several methods and materials for restoring worn, damaged or malformed teeth with porcelain restorations. Porcelain is attractive and relatively inexpensive. Porcelain restorations may be used for inlays, onlays, crowns and veneers to correct structural and/or cosmetic deficiency of teeth. Such porcelain restorations are custom made for bonding to an underlying or adjacent tooth structure.

In most recent times, there have been two basic methods for producing an all-porcelain restoration: the foil or "indirect" method and the refractory or "direct" method. In the foil method, a mold is made of the tooth structure on which the restoration is to be placed and a positive replication of the tooth structure is formed from a material poured into the mold. A platinum foil matrix is applied to and burnished over the tooth structure replication. Then, dental porcelain, in a water-based slurry, is applied over the foil matrix, baked in a furnace, ground and glazed to produce a restoration which can be bonded to the original tooth structure.

Though the foil method of producing a porcelain restoration has been proven, there are problems associated with such a method. Foil, by its nature, is difficult to completely form and adapt to the surface of a tooth structure replication and due to the fact that porcelain must be built up on the foil and must be removed from the tooth replication for subsequent firings and with the final peeling out of the foil from the finished restoration, the porcelain restorations frequently are deficient in accuracy of fit. This requires filling in with other materials so that the tooth restoration may be bonded to the original tooth structure.

The second and more accurate method of producing porcelain restorations requires the use of high heat resistant refractory investment materials molded in the shape of the tooth structure on which the tooth restoration is to be placed. The refractory investment replicates the original tooth structure and allows for direct application and subsequent firings of successive layers of dental porcelain thereto. When completed, the refractory investment is divested or removed from the finished porcelain restoration. This method, referred to as the refractory or "direct" method results in a porcelain restoration with far greater accuracy of fit.

Since porcelain has been the choice restorative for more than fifty years to replace natural teeth, it has become a common practice among dental practitioners to utilize the refractory investment method. In order to fabricate a porcelain restoration via the refractory method, a compatible porcelain must be applied to the surface of the refractory tooth replication. The commonly used porcelains conventionally used throughout the dental industry are those known as "regular" firing (1800° F.) porcelains or "low" firing (1250°–1500° F.) porcelains. Their coefficient of thermal expansion (CTE) ranges between 12 and $15 \times 10^{-6}$. These conventional porcelains are made up of crystalline materials such as feldspar, silica and kaolin. Feldspar is the major ingredient making up about 80% of the composition.

The commercially available refractory investments have worked well with these porcelains due to their matched CTE and bonding characteristics. These refractory investments contain varying grades and compositions of silica (quartz), sand, cristobalite, zirconium, magnesium and phosphate. Since the CTE between these conventionally used refractories and porcelains are suitably matched, they represent the only materials used in the refractory method throughout the industry.

There is, however, another type of porcelain available to the dental industry known as "aluminous" or high-alumina based porcelain. This type of porcelain possesses an increased strength (approx. 20,000 PSI) over conventional porcelains (approx. 10,000 PSI) due to the high percentage (50% or more) of alumina in its composition. However, the CTE of high-alumina based porcelains is approximately 6 to $7 \times 1^{-6}$. This prevents the use of conventional refractory investment materials for fabricating these high alumina based restorations.

With high-alumina porcelains, technicians have been limited to a foil or "indirect" method in which the high-alumina porcelain is applied to a platinum foil matrix which is burnished over a tooth replication made of gypsum. The foil containing the applied porcelain must then be removed from the gypsum before firing in a furnace. This procedure is time consuming, limiting in its scope of restorative types and expensive.

More recently, two other procedures have been developed to produce high-alumina dental restorations: 1) a computerized scanning machine that mills a high-alumina matrix from a block made of high-alumina material, and 2) a process that utilizes a computerized scan of a tooth to construct a tooth replication to which high-alumina particles are pressed and sintered under extreme temperatures. Both of these procedures are available but at very high expense to the industry.

Since high-alumina based porcelains possess a measurably higher strength than conventional porcelains, it would be desirable if a high-alumina restoration could be fabricated in a low cost approach via the refractory method. The reason that this has not yet occurred is due to the complete mismatch of CTE between high-alumina porcelains and existing refractory investments. This mismatch results in cracking, peeling and lifting of the porcelain off the refractory surfaces.

If refractory tooth replication materials and methods could be developed to which high-alumina porcelains would be adaptable and which would properly fire to produce an exact fitting restoration, it should be widely accepted in the industry. It's ease of production and cost effectiveness would greatly enhance the strength advantage of high-alumina porcelain restorations.

SUMMARY OF THE PRESENT INVENTION

The present invention provides materials and methods of forming a porcelain tooth restoration via the refractory method utilizing high-alumina based porcelains. By applying the high-alumina porcelain on a properly formulated refractory investment tooth replication, the tendency for the porcelain to crack or debond will be eliminated or greatly reduced.

In the method of forming a porcelain tooth restoration of the present invention, a negative impression of the tooth structure on which a tooth restoration is to be placed is prepared and a positive replication of the tooth structure is formed of the material of the present invention, an alumina-silicate based refractory investment. The material of this investment includes silica (quartz), magnesium oxide, phosphate and alumina. As stated, all prior art dental porcelain refractories contain varying amounts of silica, magnesium and phosphate, but they do not contain alumina. By adding a powdered alumina-silicate calcine in combination with silica, magnesium and phosphate, the resulting powder, when mixed with an aqueous colloidal silicate, produces a hardened positive tooth replication that will accept and match the CTE of high-alumina based porcelains.

A mixture is prepared of the alumina-silicate based refractory and aqueous hardener and poured into the negative impression of the tooth replication. After degassing and cooling the resulting positive tooth replication, a mixture of alumina-based porcelain materials may be applied and fired to finish forming the tooth restoration. Upon final firing of the tooth restoration, the alumina-silicate refractory material of the positive replication of the tooth structure may be removed, leaving the tooth restoration for etching and bonding to the tooth structure.

Thus, the materials and methods of forming a high-alumina porcelain tooth restoration of the present invention substantially eliminates incompatibilities of CTE as previously exhibited with conventional refractory investments. The new materials provide reliable refractory methods suitable for fabricating high-alumina based porcelain restorations.

DESCRIPTION OF A PREFERRED EMBODIMENT OF THE INVENTION

Figure 1:
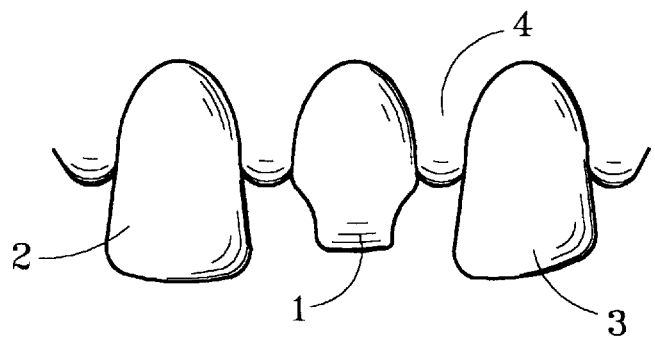
FIG. 1 is a frontal elevation view of a portion of a patient's mouth illustrating three teeth, the middle one of which is in need of restoration.

The present invention provides a method of forming porcelain tooth restorations. Such restorations include items referred to in dental practice as: inlays, onlays, crowns and veneers. The method of the present invention is suitable for forming any such items. However, for purposes of illustration, the method of the present invention will be described in forming a porcelain crown to be placed on a tooth structure 1 illustrated in FIG. 1. In FIG. 1, the tooth structure 1 is illustrated as being between two other teeth 2 and 3 extending from the gum 4 of a patient. It is presumed that the tooth structure 1 has been dentally prepared to receive a tooth restoration (crown) so that the tooth structure 1 and the crown to be placed thereon will approximate the original tooth.

The initial step of forming a porcelain restoration in the method of the present invention, as well as the prior art, is the preparation of a negative impression of the tooth structure 1 on which a tooth restoration is to be placed. This is accomplished by forming an impression of the tooth utilizing conventional mold material therefor. After the negative impression is prepared, a positive replication of the tooth structure 1 is formed in the negative impression with the high-alumina porcelain compatible refractory investment material of the present invention.

Figure 2:
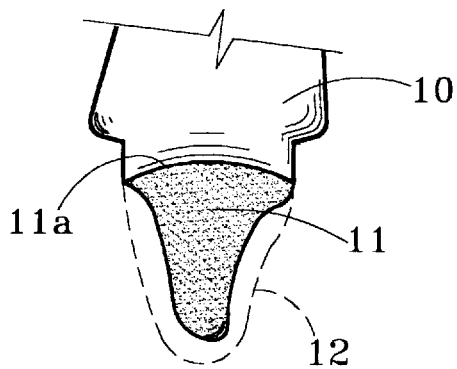
FIG. 2 represents the replication of the tooth structure of the middle tooth of FIG. 1, as viewed from the side thereof.
Figure 3:
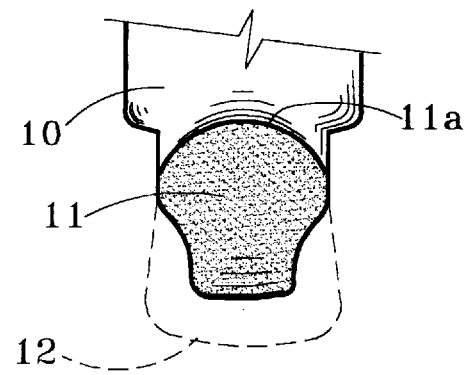
FIG. 3 represents a replication of the middle tooth structure of FIG. 1 as viewed from the front thereof.

It is at this point that the method of forming a tooth restoration of the present invention departs with the use of conventional refractory investment materials. In the method of the present invention, a formulation of a refractory investment powder made up of high-heat resistant ingredients is mixed with an aqueous colloidal silicate solution to produce the positive tooth replication 10 in FIGS. 2 and 3. The refractory powder may include components such as crystalline silica, magnesium oxide, powdered phosphate, and calcined alumina. It has been found that by adding the calcined alumina to the refractory mixture, the presence of the alumina attracts the alumina that is present in high-alumina based porcelains, thereby providing a stable "matched" CTE surface to which the high-alumina porcelain can bake and bond thereto.

The preferred formulation of refractory powder would typically include, by weight, 25% to 50% silica, 15% to 35% magnesium oxide, 10% to 25% powdered phosphate, and 10% to 30% calcined alumina. The liquid carrier for this refractory powder formulation is preferably an aqueous colloidal dispersion of silicon dioxide. A typical aqueous colloidal silicate dispersion may contain 10% to 60% silicon dioxide and 40% to 90% water.

A typical mixture may be prepared from 30 grams of the refractory powder and 7 milliliters of the aqueous dispersion. This mixture is then poured into the negative impression of the tooth restoration. After 30 minutes the mixture should be solid and may be removed from the negative impression. At this time, a thin wash of the refractory powder and aqueous dispersion may be mixed and applied over the entire positive tooth replication area 11 in FIGS. 2 and 3 except to within 3 to 5 mm of the tooth replication's margin 11a in FIGS. 2 and 3. The refractory tooth replication may then be degassed in a furnace from room temperature to approximately 2000° F.

After degassing, the tooth replication is allowed to cool to room temperature. The tooth replication may then be allowed to absorb distilled water or the replication can be coated with a liquid preparation which substantially inhibits moisture absorption prior to porcelain application. Such a preparation may be made from an aqueous colloidal dispersion of silica particles marketed under the trademark Ceralon by Cosmetex Dental International of Houston, Tex., and described in U.S. Pat. No. 5,470,231.

A mix is then prepared of a high-alumina containing core porcelain with either distilled water or a Ceralon dispersion. This mix is applied to cover the entire tooth replication area 11 of FIGS. 2 and 3. The refractory replication may then be baked in a furnace, under vacuum, from approximately 1200° F. to 2100° F. After baking the core layer, a layering build-up of alumina-based porcelain may be applied to the core surface to the shape and size of the desired restoration 12 in FIGS. 2 and 3.

Figure 4:
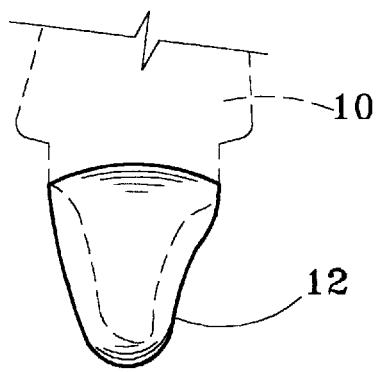
FIG. 4 represents a porcelain tooth restoration formed by the method of the present invention, as viewed from the side thereof.
Figure 5:
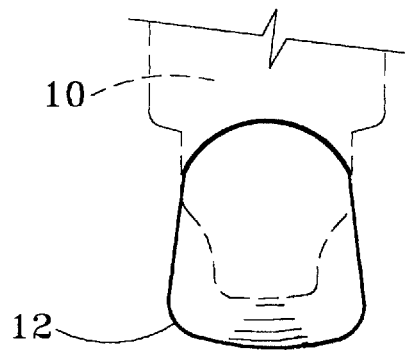
FIG. 5 represents the tooth restoration of FIG. 4 as viewed from the front thereof.

This build-up is dried and fired under vacuum according to the porcelain manufacturer's recommendations. The baked porcelain build-up may then be ground and contoured and baked again in a glaze bake to completion. The restoration, in this case a crown, is in its final shape as indicated by the dotted lines 12 in FIGS. 2 and 3. After the restoration is completed, the tooth structure replication 10 (represented by dotted lines in FIGS. 4 and 5) is removed by cutting away, sandblasting, etc. in a conventional manner. This leaves the tooth restoration 12 as in FIGS. 4 and 5 for placement on and bonding to the tooth structure 1 of FIG. 1. This tooth restoration 12 is a crackfree one of superior accuracy, possessing high-alumina strength in a much quicker and cost effective method than of the prior art.

In an alternate method, the core layer or layers of high-alumina based porcelain, after firing, may be removed from the refractory replication and placed on the gypsum replication on which the restoration would normally be sent to the dentist. The final build-up of the restoration with alumina-based porcelain would then proceed to completion.

Although materials and methods for forming high-alumina porcelain tooth restorations of the present invention have been described herein, many variations thereof can be made without departing from the spirit of the invention. Accordingly, it is intended that the scope of the invention be limited only by the claims which follow.

What is claimed is:

1. A method of forming a high-alumina based porcelain tooth restoration comprising the steps of:

preparing a negative impression of the tooth structure on which a tooth restoration is to be placed;

forming a positive replication of said tooth structure by pouring a mixture of refractory powder and aqueous dispersion into said negative impression, said refractory powder comprising 10% to 30% calcined alumina, 25% to 50% silica, 15% to 35% magnesium oxide, and 10% to 25% powdered phosphate;

allowing said positive replication to harden;

removing said positive replication from said negative impression for degassing and cooling;

coating said positive replication with a mixture of high alumina porcelain, containing 50% or more alumina, in an aqueous carrier to form a core layer of porcelain;

baking said core layer; and applying to said core layer one or more layers of high alumina porcelain, containing 50% or more alumina, to the shape and size of said tooth restoration.

2. The method of forming a high-alumina based porcelain tooth restoration as set forth in claim 1 in which said aqueous dispersion comprises 10% to 60% silicon dioxide and 40% to 90% water.

3. The method of forming a high-alumina based porcelain tooth restoration as set forth in claim 1 in which a thin wash of said refractory powder and aqueous dispersion mixture is applied to said positive replication prior to said degassing and cooling thereof.

4. The method of forming a high-alumina based porcelain tooth restoration as set forth in claim 3 in which said positive tooth replication, after said degassing and cooling thereof, is allowed to absorb distilled water prior to said high-alumina porcelain application.

5. The method of forming a high-alumina based porcelain tooth restoration as set forth in claim 3 in which portions of said positive tooth replication, after said degassing and cooling thereof, are coated with a liquid preparation which substantially inhibits moisture absorption prior to said high-alumina porcelain application.

6. The method of forming a high-alumina based porcelain tooth restoration as set forth in claim 5 in which said liquid preparation comprises an aqueous colloidal dispersion of silica particles.

7. The method of forming a high alumina based porcelain tooth restoration as set forth in claim 1 in which said positive tooth replication, after said degassing and cooling thereof, is allowed to absorb distilled water prior to said high-alumina porcelain application.

8. The method of forming a high-alumina based porcelain tooth restoration as set forth in claim 1 in which portions of said positive tooth replication, after said degassing and cooling thereof, are coated with a liquid preparation which substantially inhibits moisture absorption prior to said high-alumina porcelain application.

9. The method of forming a high-alumina based porcelain tooth restoration as set forth in claim 8 in which said liquid preparation comprises an aqueous colloidal dispersion of silica particles.

10. The method of forming a high-alumina based porcelain tooth restoration as set forth in claim 1 in which said core layer of porcelain is removed, after said baking thereof, and placed on a gypsum replication prior to final application of said one or more layers of high alumina porcelain to the shape and size of said tooth restoration.

11. The method of forming a high-alumina based porcelain tooth restoration as set forth in claim 1 in which two or more core layers are formed, baked and then removed for placement on a gypsum replication prior to final application of said one or more layers of high alumina porcelain to the shape and size of said tooth restoration.

* * * * *